United States Patent [19]

Tal et al.

[11] Patent Number: 5,366,446
[45] Date of Patent: Nov. 22, 1994

[54] INTRODUCER ASSEMBLY

[75] Inventors: Elisha A. Tal, San Francisco; Michael J. Orth, San Jose, both of Calif.

[73] Assignee: Unisurge, Inc., Cupertino, Calif.

[21] Appl. No.: 153,879

[22] Filed: Nov. 17, 1993

[51] Int. Cl.⁵ .................... A61M 5/32; A61M 5/178
[52] U.S. Cl. ................... 604/110; 604/164; 604/167; 604/256
[58] Field of Search .............. 604/164, 165, 167, 174, 604/180, 264, 256

[56] References Cited

U.S. PATENT DOCUMENTS

| | | | |
|---|---|---|---|
| 4,516,968 | 5/1985 | Marshall et al. | 604/174 |
| 4,699,616 | 10/1987 | Nowak et al. | 604/180 |
| 5,073,169 | 12/1991 | Raiken | 604/180 |
| 5,176,648 | 1/1993 | Holmes et al. | 604/180 |
| 5,215,531 | 6/1993 | Maxson et al. | 604/180 |
| 5,226,879 | 7/1993 | Ensminger et al. | 604/256 |
| 5,263,939 | 11/1993 | Wortrich | 604/174 |

*Primary Examiner*—John G. Weiss
*Attorney, Agent, or Firm*—Flehr, Hohbach, Test, Albritton & Herbert

[57] ABSTRACT

Introducer assembly for use on the skin of a patient overlying a cavity to be formed in the patient permitting the introduction of an introducer tube having a distal extremity and having a trocar therein having a distal extremity which extends beyond the distal extremity of the introducer tube. The assembly comprises a sleeve having proximal and distal extremities and having a flow passage extending therethrough from the proximal to the distal extremities. A flange having inner and outer margins is provided. The outer margin has a bottom side. An adhesive is secured to the bottom side and is adapted to make a sealing engagement with the skin of the patient. A fluid-tight seal is formed between the inner margin of the flange and the sleeve. A membrane extends across the sleeve and forms a fluid-tight seal with respect to said sleeve. The membrane is formed of a material and a thickness which can be readily punctured by the trocar. The membrane forms a substantially fluid-tight seal between the trocar as it penetrates the same and with the introducer tube after it extends through the membrane. A clamp is carried by the sleeve and is spaced from the membrane and is adapted to retain the introducer tube in a desired longitudinal position of the sleeve.

13 Claims, 2 Drawing Sheets

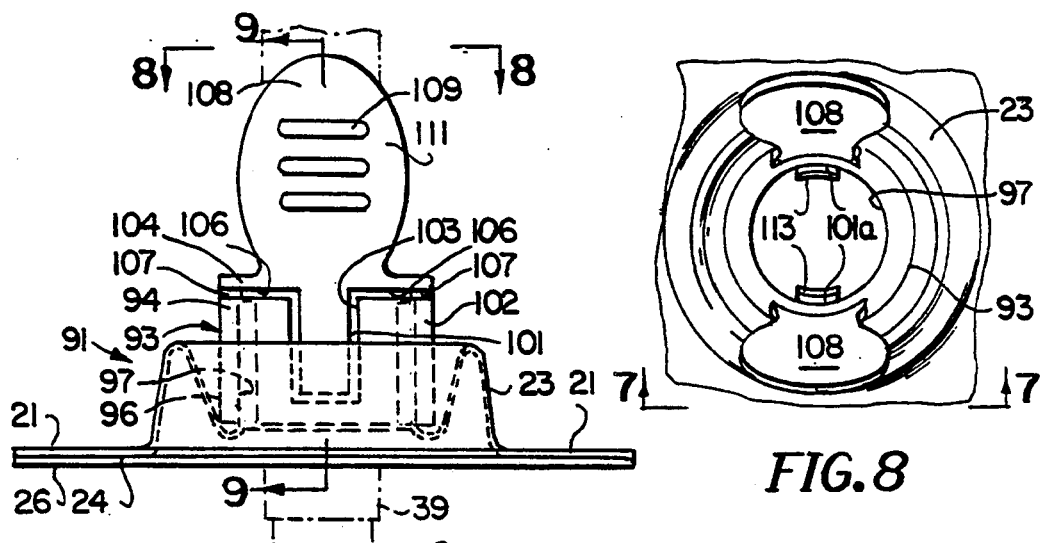
FIG.7
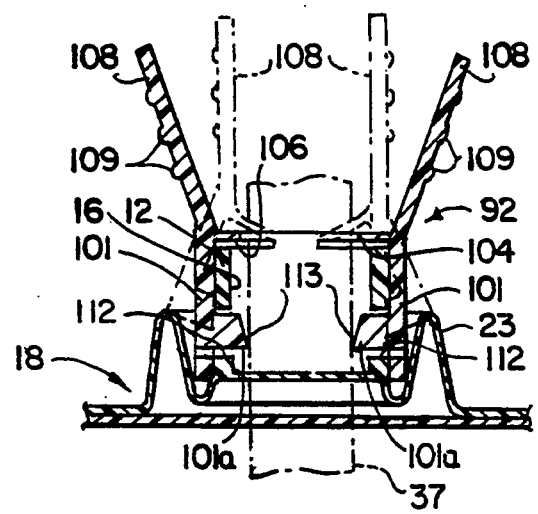
FIG.8
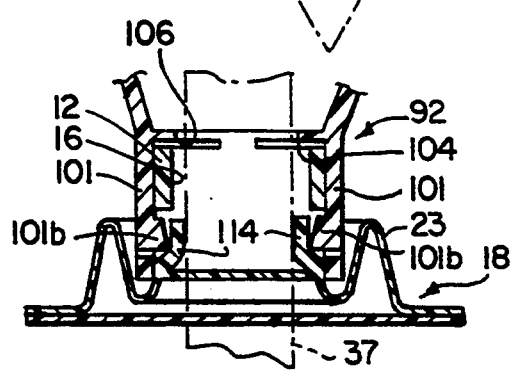
FIG.10
FIG.9
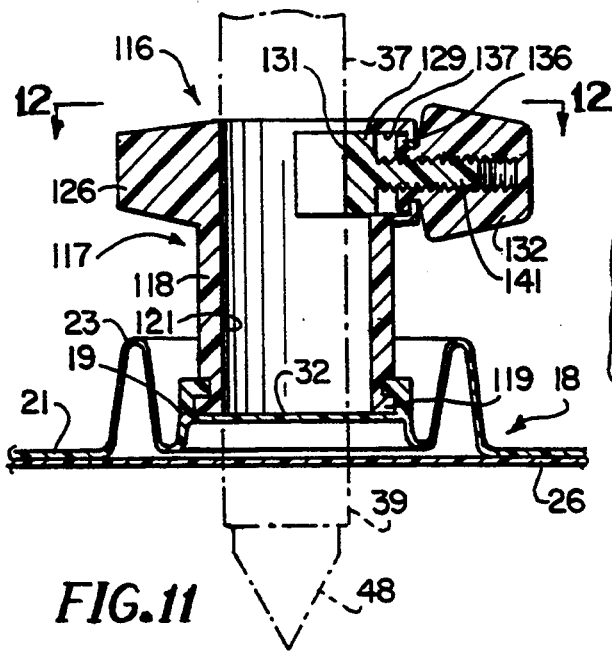
FIG.11
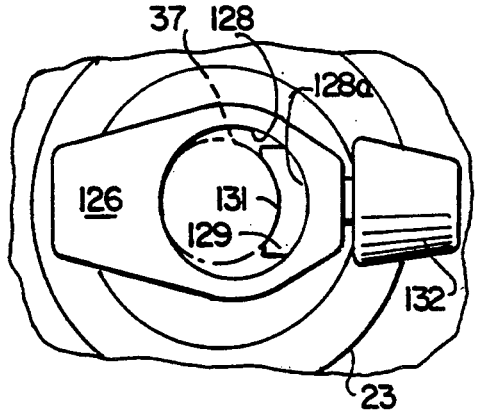
FIG.12

INTRODUCER ASSEMBLY

This invention relates to an introducer assembly and more particularly to an introducer assembly which can accommodate large variety of sizes of trocars.

In U.S. Pat. No. 5,176,648 there is disclosed an introducer assembly having many advantageous features. However, it has been found that it is unable to accommodate a large range of sizes of trocars, particularly those from other manufacturers. There is therefore need for a new and improved introducer assembly which will make it possible to utilize trocars of various sizes and from various manufacturers.

In general, it is an object of the present invention to provide an introducer assembly which can accommodate trocars of various sizes and particularly from various manufacturers.

Another object of the invention is to provide an introducer assembly which makes it possible to provide a good seal with the trocars of various sizes.

Another object of the invention is to provide an introducer assembly of the above character which has a unique clamping mechanism for accommodating trocars of various sizes.

Additional objects and features of the invention will appear from the following description in which a preferred embodiment is set forth in detail in conjunction with the accompanying drawing.

FIG. 7 is a side elevational view of an introducer assembly incorporating another embodiment of a clamping assembly for use therewith taken along the line 7—7 of FIG. 8. FIG. 8 is a top plan view taken along the line 8—8 of FIG. 7. FIG. 9 is a cross-sectional view taken along the line 9—9 of FIG. 7. FIG. 10 is a cross-sectional view similar to FIG. 9 showing an alternate construction of the introducer assembly of FIG. 7.

FIG. 11 is a cross-sectional view of another embodiment of an introducer assembly showing a different clamping mechanism.

FIG. 12 is a view looking along the line 12—12 of FIG. 11.

In general, the introducer assembly is for introduction of an introducer having an introducer tube with a distal extremity into a cavity of a patient having skin overlying the cavity for use with a trocar having a distal extremity. The introducer assembly is comprised of a sleeve having proximal and distal extremities and having a flow passage extending therethrough from the proximal to the distal extremities. A flange is provided which has inner and outer margins. The outer margin has a bottom side. Adhesive means is secured to the bottom side and is adapted to make a sealing engagement with the skin of the patient. Means is provided for forming a fluid-tight seal between the inner margin of the flange and the sleeve. Membrane means extends across the passage in the sleeve. The membrane means is capable of being penetrated by the trocar after it has been placed in the introducer with its distal extremity extending beyond the distal extremity of the introducer tube and passed at the same time through the membrane means to form a substantially fluid-tight seal between the trocar and the membrane means and thereafter between the introducer tube and the membrane means. Releasable clamping means is carried by the sleeve and is adapted to retain the introducer tube in a desired longitudinal position of the sleeve.

Figure 1:
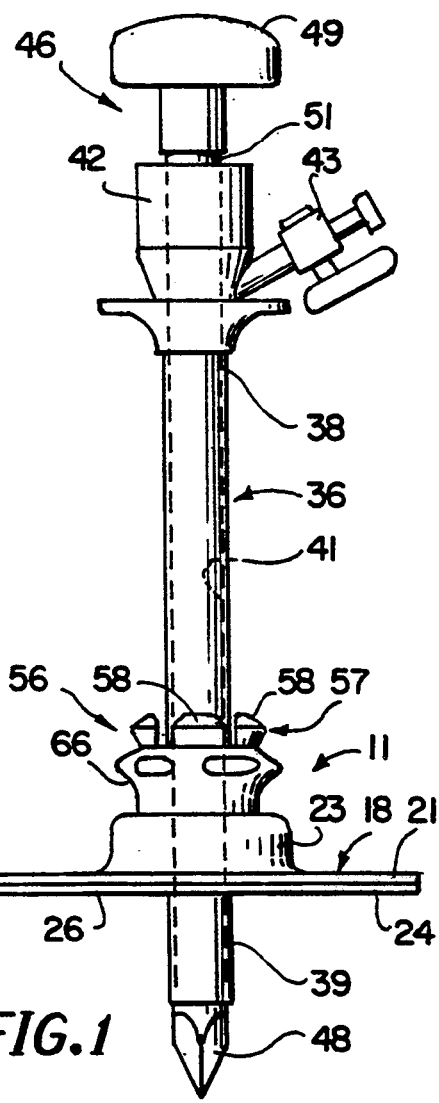
FIG. 1 is a side elevational view of an introducer assembly incorporating the present invention having a trocar disposed therein.
Figure 2:
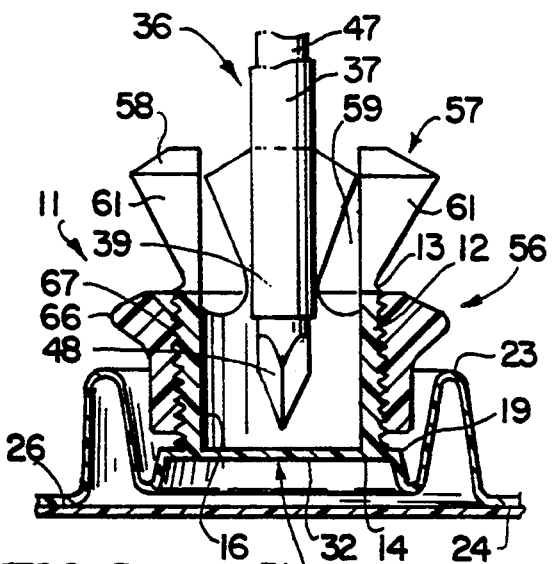
FIG. 2 is a partial cross-sectional view of an introducer assembly incorporating the present invention showing the trocar in a position to penetrate the membrane provided therein.

More particularly as shown in FIGS. 1 and 2, the introducer assembly 11 consists of a sleeve 12 which is provided with proximal and distal extremities 13 and 14. A flow passage 16 is provided in the sleeve and extends from the proximal extremity to the distal extremity 14.

A circular flange 18 generally at right angles to the axis of the flow passage 16 is provided and surrounds the sleeve 12. It has an inner margin 19 and an outer margin 1. It is also provided with an intermediate bellows-type portion 23 interconnecting the inner and outer margins 19 and 21.

The sleeve 12 can be formed of a suitable material such as plastic. The flange 18 is also formed of a suitable material such as a silicone. The outer margin 21 is provided with a lower surface 24. An adhesive (not shown) is provided on the lower surface and is adapted to make a fluid-tight seal with respect to the skin of the patient. A removable release liner 26 is secured to the lower surface 24 and extends across the flange 18. Means is provided for securing the inner margin 19 of the flange 18 to the sleeve 12 to form a fluid-tight seal therebetween, as for example it can be bonded to the distal extremity 14 of the sleeve 12 in a suitable manner, as for example by an adhesive bond.

Membrane means 31 is provided and extends across the flow passage 16 and forms a fluid-tight seal between the membrane means 31 and the sleeve 12. The membrane means 31 is in the form of a single membrane 32 formed of a suitable flexible puncturable elastomeric material such as a silicone, i.e. Krayton, which as shown extends across the distal extremity 14 and over the passage 16 and is bonded to the lower extremity of the sleeve 12 by suitable means such as an adhesive or a heat seal. It should be appreciated that if desired, the membrane 32 and the flange 18 can be formed integral with each other and be formed of the same material. To form a good seal, the elastomeric material should have a durometer ranging from 40-100 Shore A and preferably approximately 70 Shore A. It has been found that the seals which are formed are particularly effective because the gas pressures which are encountered in such cavities during the performance of surgical procedures is relatively low, as for example in the vicinity of 2 psi. The membrane can have a thickness ranging from 0.010 inches to 0.040 inches and preferably have a thickness of approximately 0.020 inches.

The introducer assembly 11 is adapted to be utilized with a introducer 36 of a conventional type which is provided with an introducer tube or cannula 37 formed of a suitable material such as plastic and is provided with proximal and distal extremities 38 and 39 with a bore 41 extending from the proximal extremity 38 to the distal extremity 39. A flange handle or head piece 42 is provided on the proximal extremity 38 and includes first and second seals (not shown) therein of a conventional type in which the first seal is typically a duckbill valve and the second seal is a ring type valve through which medical devices such as a trocar 46 can pass. The trocar 46 is of a conventional type and is provided with a shaft 47 having a sharpened distal extremity 48 and a handle 49 mounted on the proximal end 51.

A stop cock valve 43 is mounted on the head piece or handle 42 and is of a conventional type. As shown particularly in FIG. 1, the trocar 46 is adapted to be inserted into the introducer 36 with a sealing engagement being made between the trocar shaft 47 and the seals provided within the handle or head piece 42 of the introducer 36. As can be seen, the length of the introducer tube 37 and the length of the trocar shaft 47 is such that the distal extremity 48 of the trocar shaft extends at least slightly beyond the distal extremity 39 of the introducer tube 37.

Releasable clamping means 56 is carried by the sleeve. The releasable clamping means 56 can take various forms. For example, in FIGS. 1 and 2 there is shown a collet 57 which is formed with a plurality of upstanding circumferentially spaced-apart fingers 58 formed of plastic and which can be formed integral with the sleeve 12 and having slots 59 therebetween. The fingers 58 are formed with outwardly and upwardly extending tapered surfaces 61 so that the fingers have a gradually increasing thickness in a direction towards the upper extremities of the same. The collet 57 is adapted to be engaged by a collar 66 which is movable upwardly and downwardly with respect to the fingers 58 to move the fingers 58 between tool engaging and disengaging positions. This vertical movement of the collar 66 can be accomplished in various ways, as for example as shown, a threaded connection 67 can be provided between the collar 66 and the exterior surface of the sleeve 12.

It can be seen that the bore 16 provided in the sleeve 12 has a substantially larger diameter than the diameter of the introducer tube or cannula 37 so that various sizes of cannula can be utilized with the introducer assembly. Similarly, the collet 57 can be opened widely so that it can have the same size opening as the bore 16 and can be moved into engagement with the cannula or introducer tube 37 to form a sealing engagement merely by rotating the collar 66 typically in a counterclockwise direction to move it upwardly to engage the inclined surfaces 61 of the fingers to move the fingers 58 of the collet 57 into engagement with the cannula 37 to retain the cannula in a desired longitudinal position with respect to the sleeve 12. The plastic which is utilized for forming the sleeve 12 can be made of Krayton. The fingers 58 forming the collet 57 can also be formed of the same material. Alternatively it can be formed of a separate material and then bonded to the sleeve 12, however it is desirable that the fingers be flexible and be formed of a material which creates enough friction to hold the cannula in place.

Figure 3:
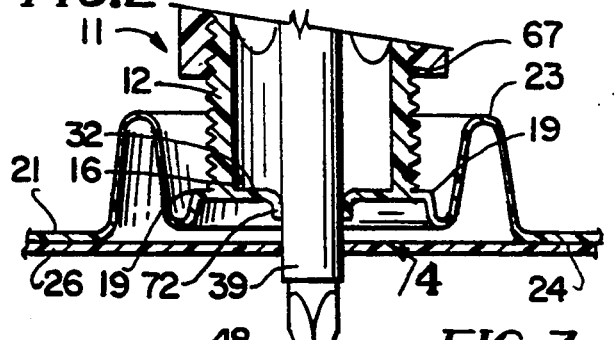
FIG. 3 is a view similar to FIG. 2 but showing the trocar after it has penetrated the membrane.

Operation and use of the introducer assembly 11 may now be briefly described as follows. Let it be assumed that it is desired to perform a surgical procedure on a patient in which it is desired to penetrate into a cavity in the patient, as for example into the abdomen of the patient by penetrating the skin overlying the cavity. With the releasable clamping means in an open position, the trocar 46 is positioned in the introducer 36 so that its distal extremity 48 extends beyond the distal extremity 39 of the introducer tube or cannula 37 and is placed in the introducer assembly 11 as shown in FIG. 2. The handle 49 of the trocar 46 is grasped by the hand and is pushed downwardly so that the distal tip 48 penetrates the membrane 32 as shown in FIG. 3. The distal extremity or tip 48 of the trocar 46 is very sharp and can easily penetrate the thin membrane 32 and in doing so creates a seal with the membrane 32 and thereafter with the introducer tube or cannula 37 as shown in FIG. 3. The three-sided sharp tip 48 of the trocar 46 cuts three slits 71 into the membrane 32 and forms three triangular-shaped flaps 72 which yieldably engage the outer surface of the cannula 37. Trocar 46 is then positioned on the abdomen in the location where it is desired to penetrate the skin of the patient to obtain access to a cavity underlying the skin and is then inserted into the cavity. Release liner 26 of introducer assembly 11 is then removed and the adhesive carried by the lower surface 24 of the outer margin 21 of the flange 18 is pressed onto the skin of the patient around the incision made by the trocar.

Figure 4:
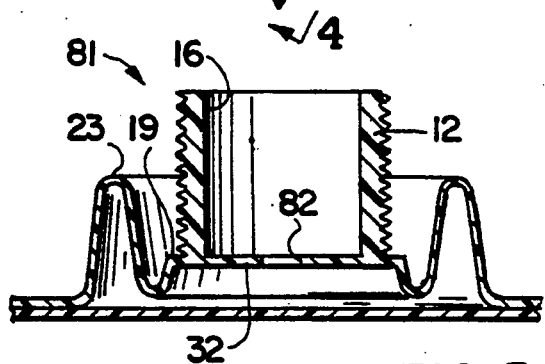
FIG. 4 is a view looking along the line 4—4 of FIG. 3.
Figure 4:
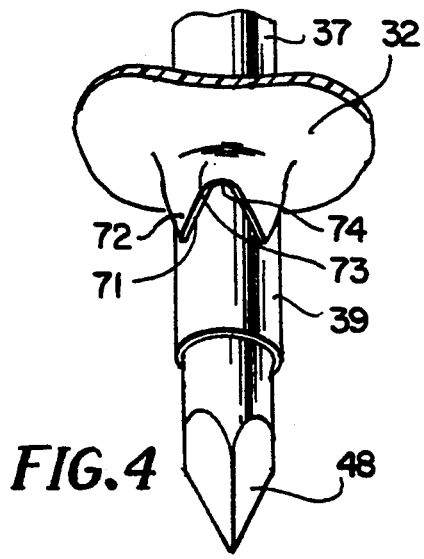

As shown particularly in FIG. 4, the puncturing of membrane 32 creates an inner margin 73 extending inwardly from the apices 74 of the v-shaped slots 71 to form a substantially liquid-tight seal between the membrane 32 and the exterior surface of the cannula 37. It can be seen that by trocar 46 puncturing membrane 32, the membrane can accommodate various sizes of cannula and still provide a substantially fluid-tight seal between the membrane 32 and the cannula 37.

Thus it can be seen that when a trocar and a cannula are introduced through the membrane they form a fluid-tight seal between the cannula and the membrane regardless of the size of the cannula. An effective valve is created by utilizing a membrane to create a seal around the tool which makes the puncture through the membrane. This good seal is formed because the membrane is formed of an elastomeric material.

Figure 5:
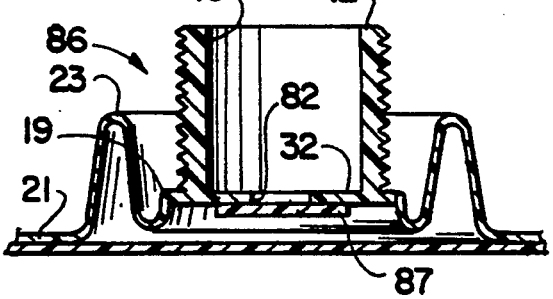
FIG. 5 is a cross-sectional view of another embodiment of an introducer assembly incorporating the present invention.

Another embodiment of an introducer assembly 81 incorporating the present invention is shown in FIG. 5. It is substantially identical to the introducer assembly 11 hereinbefore described with the exception that the membrane 32 is provided with a centrally disposed small starter hole 82 in which the membrane 32 is to be utilized with trocars ranging in diameter from 0.020 inches to 0.550 inches. With such large diameter trocars it may desirable to utilize a starter hole or aperture 82 having the diameter in the range of 0.100 to 0.150 inches which would still make it necessary for the trocar to make the triangular cuts hereinbefore described to create the flaps. However, because of the starter hole, the flaps would not need to be as long. By providing such a starter hole it takes less force to have the trocar penetrate the membrane to form the triangular-cut pattern while at the same time making it easier to utilize the introducer assembly 81 with a large variation in diameters of the trocars.

Figure 6:
FIG. 6 is a cross-sectional view of still another embodiment of an introducer assembly incorporating the present invention.

Still another embodiment of an introducer assembly 86 incorporating the present invention is shown in FIG. 6 which is very similar to the introducer assembly shown in FIGS. 1, 2 and 5 with the exception that a secondary membrane 87 has been provided which underlies the membrane 32 and the starter hole 82 therein. This secondary membrane 87 can be secured to the membrane 32 by suitable means such as an adhesive or a heat seal. It can be formed of the same material as the membrane 32 or alternatively it can be formed of a different material at a thickness to give the desired sealing characteristics. For example, it can be made thinner or thicker than the seal 32. It also can be provided with different elastomeric qualities.

Another embodiment of an introducer assembly 91 incorporating the present invention is shown in FIGS. 7 through 9 in which, as in the previous embodiments, the clamping assembly 92 is separated from the seal formed by the membrane 32.

The introducer assembly 91 is provided with a sleeve 93 formed of a suitable material such as ULTEM with the clamping assembly 92 being formed as an integral part therewith. The sleeve 93 is provided with proximal and distal extremities 94 and 96 and has a flow passage 97 extending therethrough. Sleeve 93 is concentrically carried about the outside of sleeve 12 and is secured thereto by an suitable means such as bonding (see FIGS. 7 and 9).

Clamping assembly 92 is formed by a pair of spring loaded members or fingers 101 which are formed from the wall 102 of the sleeve 93 by cutting a U-shaped slot 103 in the wall 102. The fingers 101 are formed integral with semicircular ring portions 104 which are formed by cutting arcuate slots 106 on opposite sides of the fingers 101. The slots 106 subtend an angle of at least 75° so that there remains a pair of diametrically opposed posts 107 which connect the ring portions 104 to the remainder of the wall 102. Also formed integral with the ring portion 104 are upwardly and outwardly extending finger means or members 108 which are generally oval-shaped as shown and which are provided with laterally extending rounded protrusions 109 on the outer surface 111 adapted to be engaged by the fingers of a hand. The ring portions 104 serve as hinge points for the fingers 101 as the finger members 108 are pinched or brought together into the broken lined positions shown in FIG. 9. The fingers 101 are provided with inwardly extending finger portions 101a which extend through openings 112 provided in sleeve 12 into flow passage 16 of the sleeve. Finger portions 101a are provided with inclined surfaces 113 that are adapted to frictionally engage a cannula 37 inserted therebetween.

Typically as shown when the cannula 37 is introduced through the clamping assembly 92, the finger members 108 are grasped by the fingers of the hand and are pushed inwardly towards each other to bring the spring member portions 101a outwardly to permit the passage of the cannula 37 therethrough. As soon as the cannula 37 has been positioned in the desired position, the fingers 108 can be released and the yieldable forces provided by the plastic material forming the ring portions 104 urges the outer surfaces 113 to engage the outer surface of the cannula 37 to frictionally retain the same in a desired longitudinal position within the passage 97 of the sleeve 93. To reposition the cannula 37 it is merely necessary to use the fingers of the hand to grasp the finger members 108 and to pinch them together to permit the cannula 37 to be repositioned after which the finger members 108 can be released to again frictionally retain the cannula 37 in the desired longitudinal position in the sleeve 93. Should fingers 101 be pivoted outwardly so as to engage portions 23 of circular flange 18, the opposing force of the flange on fingers 101 will assist in the frictional engagement between inclined surfaces 113 and cannula 37. The membrane 32 also applies friction forces to provide additional fixation. The clamping assembly 92 has the advantage in that it can be pinched open with a single hand whereas the clamping means 56 hereinbefore described requires the use of two hands, one for the sleeve 12 and the other for twisting the collar 66.

In an alternate embodiment of introducer assembly 91 which is shown in FIG. 10, fingers 101 have inwardly extending finger portions 101b which are shorter than finger portions 101a and engage flaps 114 formed in sleeve 12. Finger portions 101b serve to urge flaps 114 against cannula 37 and frictionally retain the cannula in the desired longitudinal position. The Krayton material of flaps 114 has a higher coefficient of friction than the material of sleeve 93 and finger portions 101b thereof and thereby provides for higher frictional forces than those between finger portion 101b and the cannula.

Still another embodiment of an introducer assembly 116 incorporating the present invention is shown in FIGS. 11 and 12 and consists of a sleeve 117 made from a suitable material such as ULTEM. Sleeve 117 has proximal and distal extremities 118 and 119 and a flow passage 121 extending therethrough. A flange 18 having an integral membrane 32 of the type hereinbefore described is secured to distal extremity 119 so that membrane 32 closes off the passage 121. A flange 126 is formed integral with the proximal extremity 118 and is provided with a hole 128 which is generally in registration with the flow passage 21 but which has an offset portion 128a which has disposed therein a clamping member 129. The clamping member 129 is provided with an arcuate surface 131 which is adapted to engage the cannula 37.

Means is provided for moving the arcuate member 129 toward the side of the opening 128 so that it can engage a cannula 37 inserted therethrough and consists of a knob 32 which is rotatably mounted in the flange 126 and is retained therein by means of a small radially extending flange 136 mounted in a circular recess 137 provided along the side of flange 126. The arcuate member 129 is provided with a threaded extension 141 which threadedly engages the knob 132 as shown in FIG. 11 whereby as the knob 132 is rotated, the arcuate member 121 is advanced and retracted across the passage 121 to thereby frictionally engage a cannula inserted therethrough or to release the same. The clamping assembly shown in FIGS. 11 and 12 has the advantage in that it is relatively simple. However, it has a disadvantage that the cannula being clamped is moved off center. However this off center movement can be readily accommodated by the membrane 32.

It can be seen from the foregoing that there has been provided an introducer assembly of various types which can be utilized for readily accommodating cannula and trocars used therewith of various sizes while maintaining a good seal between the trocar and the cannula as well as providing separate means separate from the sealing means for adjustably positioning the cannula longitudinally of the sleeve. By providing such an introducer assembly, it is possible to readily accommodate the cannula of different manufacturers. Although the membrane type seals provided herein only permit one time use, this is not a disadvantage since typically such introducer assemblies are disposed of after use. Such an introducer assembly is still cost effective because it is relatively small and can be manufactured relatively inexpensively.

We claim:

1. Introducer assembly for use on the skin of a patient overlying a cavity to be formed in a patient permitting the introduction of any one of a variety of introducer tubes having different outer diameters and forming a substantially fluid-tight seal with the introducer tube, each introducer tube having a distal extremity and having a trocar therein having a distal extremity which extends beyond the distal extremity of the introducer tube, comprising a sleeve having proximal and distal extremities and having a passage extending therethrough from the proximal to the distal extremities, the diameter of the passage being at least as great as the outer diameter of the largest introducer tube to be introduced therethrough a flange having inner and outer margins, said outer margin having a bottom side adapted to make a sealing engagement with the skin of the patient, means forming a fluid-tight seal between the inner margin of the flange and the sleeve, membrane means extending across the passage and forming a fluid-tight seal with respect to said sleeve, said membrane means being formed of a material and having a thickness which can be readily pierced by the trocar of the selected introducer tube and which forms a substantially fluid-tight seal with the trocar as it penetrates the same and with the selected introducer tube after it extends through the membrane means, and releasable clamping means carried by the sleeve and spaced from the membrane means adapted to receive the selected introducer tube and adapted to retain the selected introducer tube in a desired longitudinal position of the sleeve.

2. An introducer assembly as in claim 1 wherein said passage in the sleeve has a diameter which is substantially greater than the outer diameter of the introducer tube.

3. A introducer assembly as in claim 1 wherein said membrane means is formed of an elastomeric material with a thickness ranging from 0.010 to 0.040 inches.

4. An introducer assembly as in claim 1 wherein said membrane means is provided with a centrally disposed small aperture.

5. An introducer assembly as in claim 4 together with an additional membrane means extending across said first named membrane means and covering said small aperture in said first named membrane means.

6. An introducer assembly as in claim 1 wherein said membrane means as it is penetrated by said trocar produces triangularly shaped flaps which yieldably engage the surface of the introducer tube to form a fluid-tight seal therewith.

7. An introducer assembly as in claim 1 wherein said clamping means comprises a collet of upwardly extending spaced apart fingers secured to said sleeve and collar means carried by said collet for moving said fingers of said collet between introducer tube engaging and disengaging positions.

8. An introducer assembly as in claim 7 wherein said fingers increase in thickness in an upward direction and have an outer inclined surface engaged by the collar.

9. An introducer assembly as in claim 8 wherein said collar is threadedly mounted on said sleeve.

10. An introducer assembly as in claim 1 wherein said clamping means comprises first and second spring fingers, means carried by the sleeve for carrying said spring fingers and for yieldably urging the spring fingers in a direction into the passage to engage an introducer tube extending through the passage and finger means carried by the spring fingers for moving the spring fingers in a direction against the yieldable force to move the spring fingers from an introducer tube engaging position.

11. An introducer assembly as in claim 10 wherein said spring fingers and said means for carrying said spring fingers are formed integral with the sleeve.

12. An introducer assembly as in claim 1 wherein said clamping means comprises a clamping member for frictionally engaging the introducer tube movable transversely of the passage and screw means carried by the sleeve for moving the clamping member into and out of engagement with an introducer tube.

13. An introducer assembly as in claim 1 wherein said membrane means forms a substantially fluid-tight seal with trocars having outer diameters ranging from approximately 0.020 inch to 0.550 inch.

* * * * *